United States Patent [19]

Pool

[11] 4,272,823
[45] Jun. 9, 1981

[54] CONTROL SYSTEM FOR A REACTOR

[75] Inventor: Joe V. Pool, Bartlesville, Okla.

[73] Assignee: Phillips Petroleum Company, Bartlesville, Okla.

[21] Appl. No.: 88,716

[22] Filed: Oct. 26, 1979

[51] Int. Cl.³ .............................................. G06G 7/58
[52] U.S. Cl. ................................ 364/500; 23/230 A;
208/156; 208/DIG. 1; 422/109; 422/110;
422/142; 364/109
[58] Field of Search ............... 364/109, 500, 501, 502,
364/118; 422/108, 109, 110, 110, 111, 62, 142;
23/230 A; 208/DIG. 1, 143, 155, 156;
423/DIG. 5; 585/259, 263, 261, 265

[56] References Cited

U.S. PATENT DOCUMENTS

| | | | |
|---|---|---|---|
| 3,228,858 | 1/1966 | Matyear et al. ................. | 422/110 X |
| 3,441,626 | 4/1969 | Kelley ............................ | 208/143 X |
| 3,497,449 | 2/1970 | Urban ............................. | 364/109 X |
| 3,607,091 | 9/1971 | Boyd ......................... | 208/DIG. 1 X |
| 3,725,653 | 4/1973 | Carr et al. .................. | 208/DIG. 1 X |
| 3,748,448 | 7/1973 | Sayles et al. ............... | 208/DIG. 1 X |
| 3,974,064 | 8/1976 | Bajek et al. ................ | 208/DIG. 1 X |
| 3,979,183 | 9/1976 | Scott .......................... | 208/DIG. 1 X |
| 3,981,793 | 9/1976 | Christie et al. ............ | 208/DIG. 1 X |
| 4,069,413 | 1/1978 | Rutledge et al. ................... | 364/118 |
| 4,100,266 | 7/1978 | Smith .............................. | 422/108 X |

*Primary Examiner*—Joseph F. Ruggiero

[57] ABSTRACT

Control of the temperature profile across a reactor which contains a plurality of catalyst beds is accomplished by splitting the feed to the reactor in such a manner that a portion of the feed is introduced into the first catalyst bed in the reactor and the remainder of the feed is introduced into the second catalyst bed of the reactor. The temperature of the feed stream introduced into the first catalyst bed in the reactor is manipulated so as to maintain a desired temperature in the first catalyst bed. The feed stream introduced into the second catalyst bed of the reactor is utilized to cool the effluent flowing from the first catalyst bed to maintain a desired temperature in the second catalyst bed. A recycle stream is introduced into the remaining catalyst beds with the flow rate of the recycle stream being manipulated so as to maintain desired temperatures in the remaining catalyst beds.

Control of the ratio of the reactants flowing to the reactor is accomplished by analyzing both the feed stream to the reactor and the reaction effluent flowing from the reactor to derive a set point which is utilized to control the flow rate of at least one of the reactants to the reactor so as to maintain a desired ratio of the reactants in the reactor.

16 Claims, 1 Drawing Figure

FIGURE 1

CONTROL SYSTEM FOR A REACTOR

This invention relates to control of a reactor. In one aspect this invention relates to method and apparatus for controlling the temperature profile across a reactor which contains a plurality of catalyst beds in series. In another aspect this invention relates to method and apparatus for controlling the ratio of the reactants in the feed stream flowing to the reactor.

Many chemical processes employ reactors which contain a plurality of catalyst beds in series. It is important to be able to control the temperature of each catalyst bed to thereby control the temperature profile across the reactor so as to insure maximum conversion of the reactants to a desired product and to also insure that dangerous temperature levels are not reached.

It is thus an object of this invention to provide method and apparatus for controlling the temperature profile across a reactor which contains a plurality of catalyst beds in series.

Generally, the feed stream to a reactor will contain a plurality of reactants. It is important to be able to control the ratio of the reactants to each other to insure maximum conversion to a desired product and also insure that reactants will not be wasted. Many times the control of the ratio of the reactants will be important to prevent undesired side reactions. Also the ratio of the reactants should be controlled so as to limit the unreacted reactants in the effluent flowing from the reactor so as to simplify subsequent separation processes.

It is thus an object of this invention to provide method and apparatus for controlling the ratio of the reactants in the feed stream flowing to a reactor.

In accordance with the present invention, method and apparatus is provided whereby the temperature profile across a reactor containing a plurality of catalyst beds in series is controlled by introducing at different points in the reactor, a plurality of streams having different temperatures. The feed stream containing the reactants is split prior to introducing the feed stream into the reactor. A first portion of the feed stream is introduced into the feed inlet of the reactor and flows through the first catalyst bed. The temperature of this first portion of the feed stream is manipulated so as to maintain a desired inlet temperature to the first catalyst bed. The second portion of the feed stream is introduced into the reactor downstream of the first catalyst bed and in front of the second catalyst bed and is combined with the reaction effluent flowing from the first catalyst bed. The cooling effect of this second portion of the feed stream produces a desired inlet temperature to the second catalyst bed. A recycle stream from the separation process for the reaction effluent flowing from the reactor is provided to the remaining catalyst beds. This recycle stream can be split into as many streams as there are remaining catalyst beds. The flow rate of each separate recycle stream is manipulated to maintain a desired inlet temperature to the catalyst bed into which the recycle stream is introduced. In this manner, the temperature profile across the reactor is controlled.

An analysis of the reaction effluent flowing from the reactor is utilized to establish a signal which is responsive to the difference between the actual ratio of the reactants remaining in the reaction effluent and the desired ratio of the reactants remaining in the reaction effluent. This difference signal is scaled so as to be representative of the desired ratio of the reactants in the feed flowing to the reactor. An analysis of the feed flowing to the reactor is utilized to establish a signal which is representative of the actual ratio of the reactants in the feed flowing to the reactor. This actual ratio is compared to the desired ratio and the flow rate of at least one of the reactants is controlled in response to this comparison to thus maintain a desired ratio of the reactants in the feed stream flowing to the reactor.

Other objects and advantages of the invention will be apparent from the foregoing brief description of the invention and from the claims as well as the detailed description of the drawing in which:

The invention is described in terms of a process for producing methyl t-butyl ether. However, the invention is applicable to other chemical processes where it is desired to maintain a desired temperature profile across a reactor containing a plurality of catalyst beds and/or it is desired to maintain a desired ratio of reactants in the feed stream flowing to a reactor. The control of the temperature profile across a reactor is also applicable to processes where only a single reactant is flowing to a reactor. The reactant ratio control of the present invention is applicable to any reactor to which a feed stream containing at least two reactants is supplied.

The invention is described in terms of using the overhead streams from a fractionator associated with a process for producing methyl t-butyl ether as the diluent fluid. However, any suitable diluent fluid from any suitable source may be utilized if desired.

Although the invention is illustrated and described in terms of a specific reactor and a specific control system for the reactor, the invention is also applicable to different types and configurations which accomplish the purpose of the invention. Lines designated as signal lines in the drawings are electrical or pneumatic in this preferred embodiment. However, the invention is also applicable to mechanical, hydraulic or other signal means for transmitting information. In almost all control systems some combination of these types of signals will be used. However, use of any other type of signal transmission, compatible with the process and equipment in use is within the scope of the invention.

The controllers shown may utilize the various modes of control such as proportional, proportional-integral, proportional-derivative, or proportional-integral-derivative. In this preferred embodiment, proportional-integral controllers are utilized but any controller capable of accepting two input signals and producing a scaled output signal, representative of a comparison of the two input signals, is within the scope of the invention. The operation of proportional-integral controllers is well known in the art. The output control signal of a proportional-integral controller may be represented as $$S = K_1 E + K_2 \int E \, dt$$

where
 $S$ = output control signals;
 $E$ = difference between two input signals;
 $K_1$ and $K_2$ = constants.

The scaling of an output signal by a controller is well known in control systems art. Essentially, the output of a controller may be scaled to represent any desired factor or variable. An example of this is where a desired pressure and an actual pressure is compared by a controller. The output could be a signal representative of a desired change in the flow rate of some gas necessary to make the desired and actual pressures equal. On the other hand, the same output signal could be scaled to represent a percentage or could be scaled to represent a temperature change required to make the desired and actual pressures equal. If the controller output can range from 3 to 15 pounds, which is typical, then the output signal could be scaled so that an output signal having a pressure of 9 pounds corresponds to 50 percent, some specified flow rate, or some specified temperature.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more of such equipment types. While the presently preferred embodiment of the invention preferably utilizes a combination of pneumatic control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. In addition, all signals could be translated into a "suppressed zero" or other similar format in order to provide a "live zero" and prevent an equipment failure from being erroneously interpreted as a "low" or "high" measurement or control signal. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Figure 1:
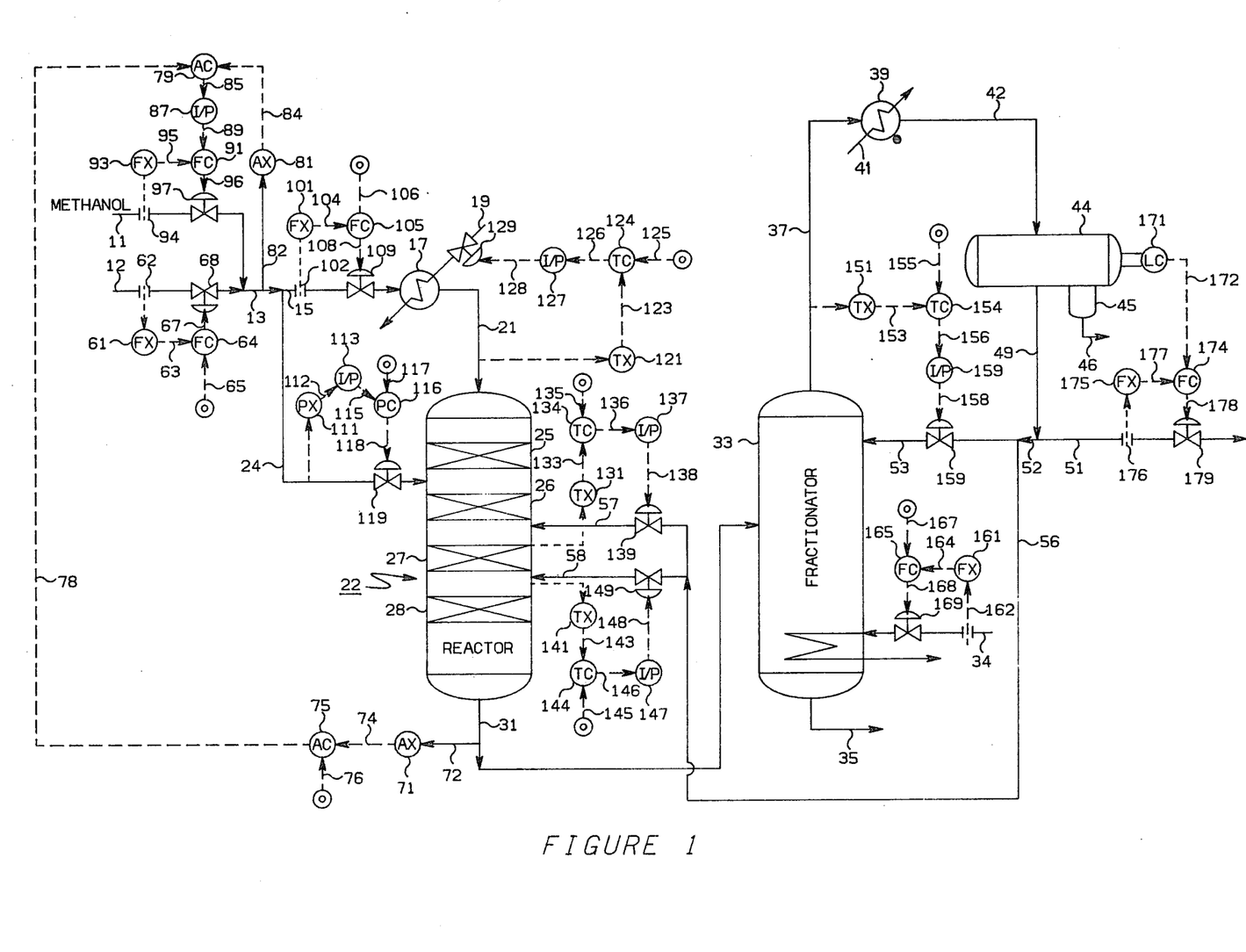
FIG. 1 is a diagrammatic illustration of a reactor in series with a fractionator and an associated control system for the reactor and fractionator.

Referring now to FIG. 1, an alcohol which is preferably methanol is provided through conduit means 11. An isobutylene containing feed stream is provided through conduit means 12. The isobutylene containing stream flowing through conduit means 12 will typically be the $C_4$ stream from a catalytic cracker. The feed flowing through conduit means 11 and the feed flowing through conduit means 12 are combined and flow through conduit means 13. A portion of the feed flowing through conduit means 13 is provided through conduit means 15 to the heat exchanger 17. The heat exchanger 17 is provided with a heating fluid through conduit means 19. After being heated, the feed flowing through conduit means 15 is provided from the heat exchanger 17 through conduit means 21 to the reactor 22. The portion of the feed stream flowing through conduit means 13 which does not flow to the heat exchanger 17 is provided through conduit means 24 to the reactor 22. The reactor 22 contains four catalyst beds $25 \cong 28$. Any suitable catalyst can be utilized in the catalyst beds 25–28. Preferably, Amberlyst 15 which is an ion exchange resin obtainable from Rohm and Haas is the catalyst utilized. The catalyst beds 25–28 are in series in such a manner that reactants flow from catalyst bed 25 into catalyst bed 26. From catalyst bed 26 the reactants flow through catalyst bed 27 and then through catalyst bed 28 and out of the reactor. The feed flowing through conduit means 21 is introduced into catalyst bed 25. The feed flowing through conduit means 24 is introduced prior to catalyst bed 26 but after catalyst bed 25.

The reaction effluent from the reactor 22 is withdrawn from the reactor 22 through conduit means 31. The reaction effluent will typically contain methyl t-butyl ether together with some methanol, isobutylene and other constituents of the feed flowing to the reactor 22 which do not react to form methyl t-butyl ether. The reaction effluent from the reactor 22 flows through conduit means 31 and is introduced as a feed into the fractionator 33. The fractionator 33 is utilized to split the methyl t-butyl ether from the other constituents of the effluent stream flowing through conduit means 31.

Heat is supplied to the fractionator 33 by a heating fluid which flows through conduit means 34. Methyl t-butyl ether is removed from the fractionator 33 as a bottoms product through conduit means 35. The remaining constituents of the reaction effluent flowing through conduit means 31 are removed as an overhead product from the fractionator 33 through conduit means 37. The overhead stream flowing through conduit means 37 is provided to the heat exchanger 39. A cooling fluid is provided to the heat exchanger 39 through conduit means 41. The thus cooled overhead stream flowing through conduit means 37 flows from the heat exchanger 39 through conduit means 42 to the overhead accumulator 44. The overhead accomulator 44 has a knockout pot 45. Typically, methanol and any water contained in the overhead stream flowing through conduit means 42 will accumulate in the knockout pot 45 and will be removed through conduit means 46. The liquid portion of the overhead stream flowing through conduit means 42 which is not removed through conduit means 46 flows from the overhead accumulator 44 through conduit means 49. A portion of the fluid flowing through conduit means 49 is removed through conduit means 51. The remaining portion of the fluid flowing through conduit means 49 is provided either to the fractionator 33 through the combination of conduit means 52 and 53 or to the reactor 22 through the combination of conduit means 52 and 56–58. In particular, the effluent flowing through conduit means 57 is provided to the reactor 22 prior to the third catalyst bed 27 but after the second catalyst bed 26. The fluid flowing through conduit means 58 is provided to the reactor 22 prior to the fourth catalyst bed 28 but after the third catalyst bed 27.

Flow transducer 61 in combination with flow sensor 62, which is operably located in conduit means 12, provides an output signal 63 which is representative of the flow rate of the feed flowing through conduit means 12. Signal 63 is provided as a first input to the flow controller 64. The flow controller 64 is also provided with a set point signal 65 which is representative of the desired flow rate of the feed flowing through conduit means 12. In response to signals 63 and 65, the flow controller 64 establishes an output 67 which is responsive to the difference between signals 63 and 65. Signal 67 is provided as a control signal to the pneumatic control valve 68 which is operably located in conduit means 12. The pneumatic control valve 68 is manipulated in response to signal 67 to thereby maintain the actual flow rate of the feed flowing through conduit means 12 substantially equal to the desired flow rate represented by signal 65.

Analyzer transducer 71, which is preferably a chromatographic analyzer, is operably connected to conduit means 31 through conduit means 72. Analyzer transducer 71 analyzes the concentration of the methanol and the isobutylene in the reaction effluent flowing through conduit means 31 and establishes an output signal 74 which is representative of the ratio of the methanol to the isobutylene. Signal 74 is provided from the analyzer transducer 71 as a first input to the analyzer controller 75. The analyzer controller 75 is also provided with a set point signal 76 which is representative of the desired ratio of the methanol to isobutylene in the reaction effluent flowing through conduit means 31. In response to signals 74 and 76, the analyzer controller 75 establishes an output signal 78 which is responsive to the difference between signals 74 and 76. Signal 78 is scaled so as to be representative of the ratio of methanol to isobutylene in the feed flowing through conduit means 13 which is required to maintain the ratio of methanol to isobutylene in the reaction effluent flowing through conduit means 31 substantially equal to the ratio represented by the set point signal 76. Signal 78 is provided from the analyzer controller 75 as the set point signal to the analyzer controller 79.

Analyzer transducer 81, which is preferably a chromatographic analyzer, is operably connected to conduit means 13 through conduit means 82. Analyzer transducer 81 analyzes the concentration of the methanol and the concentration of the isobutylene in the feed flowing through conduit means 13. Analyzer transducer 81 then establishes an output signal 84 which is representative of the ratio of methanol to isobutylene in the feed flowing through conduit means 13. Signal 84 is provided from the analyzer transducer 81 to the analyzer controller 79. In response to signals 78 and 84, the analyzer controller 79 establishes an output signal 85 which is responsive to the difference between signals 78 and 84. Signal 85 is provided from the analyzer controller 79 to the current-to-pressure (I/P) transducer 87. Signal 85 is converted from electrical form to pneumatic form and is provided as signal 89 to the flow controller 91. Signal 85 will be scaled so as to be representative of the flow rate of the methanol required to maintain a desired ratio of methanol to isobutylene in the reaction effluent flowing through conduit means 31.

Flow transducer 93, in combination with flow sensor 94 which is operably located in conduit means 11, provides an output signal 95 which is representative of the flow rate of the methanol flowing through conduit means 94. Signal 95 is provided as the process variable input to the flow controller 91. In response to signals 89 and 95, the flow controller 91 establishes an output signal 96 which is responsive to the difference between signals 89 and 95. Signal 96 is provided from the flow controller 91 as a control signal to the pneumatic control valve 97 which is operably located in conduit means 11. The pneumatic control valve 97 is manipulated in response to signal 96 to thereby maintain the desired ratio of methanol to isobutylene in the feed flowing to the reactor 22.

Flow transducer 101, in combination with flow sensor 102 which is operably located in conduit means 15, provides an output signal 104 which is representative of the flow rate of the feed flowing through conduit means 15. Signal 104 is provided as the process variable input to the flow controller 105. The flow controller 105 is also provided with a set point signal 106 which is representative of the desired flow rate of the feed flowing through conduit means 15. Signal 106 will typically be a value which will provide a desired split of the feed flowing through conduit means 13 between conduit means 15 and conduit means 24.

In response to signals 104 and 106, the flow controller 105 establishes an output signal 108 which is responsive to the difference beteen signals 104 and 106. Signal 108 is provided from the flow controller 105 as a control signal to the pneumatic control valve 109 which is operably located in conduit means 15. The pneumatic control valve 109 is manipulated in response to signal 108 to thus provide a desired split of the feed flowing through conduit means 13.

Pressure transducer 111, in combination with a pressure sensing device which is operably located in conduit means 24, provides an output signal 112 which is representative of the pressure of the feed flowing through conduit means 24. Signal 112 is provided from the pressure transducer 111 as an input to the I/P transducer 113. Signal 112 is converted from electrical form to pneumatic form by the I/P transducer 113 and is provided as signal 115 to the pressure controller 116. The pressure controller 116 is also provided with a set point signal 117 which is representative of the desired pressure of the feed flowing through conduit means 24. In response to signals 115 and 117, the pressure controller 116 establishes an output signal 118 which is responsive to the difference between signals 115 and 117. Signal 118 is provided as a control signal to the pneumatic control valve 119 which is operably located in conduit means 24. The pneumatic control valve 119 is manipulated in response to signal 118 to thereby maintain a desired pressure of the feed flowing through conduit means 24.

Typically, the set point for the pressure controller will remain at some constant value and the set point for the flow controller 105 will be utilized to provide the desired split of the feed flowing through conduit means 13.

Temperature transducer 121, in combination with a temperature sensing device such as a thermocouple which is operably located in conduit means 21, provides an output signal 123 which is representative of the feed inlet temperature of the reactor 22 or the inlet temperature to catalyst bed 25. Signal 123 is provided as the process variable input to the temperature controller 124. The temperature controller 124 is also provided with a set point signal 125 which is representative of the desired feed inlet temperature of the reactor 22. In response to signals 123 and 125, the temperature controller 124 establishes an output signal 126 which is responsive to the difference between signals 123 and 125. Signal 126 is provided from the temperature controller 124 as an input to the I/P transducer 127. Signal 126 is converted from electrical form to pneumatic form by the I/P transducer 127 and is provided as signal 128 to the pneumatic control valve 129 which is operably located in conduit means 19. The pneumatic control valve 129 is manipulated in response to signal 128 to thereby maintain the inlet temperature of the catalyst bed 25 substantially equal to the desired inlet temperature represented by the set point signal 125.

Temperature transducer 131, in combination with a temperature sensing device such as a thermocouple which is operably located in the reactor 22, provides an output signal 123 which is representative of the inlet temperature of the catalyst bed 27. Signal 133 is provided as the process variable input to the temperature controller 134. The temperature controller 134 is also provided with a set point signal 135 which is representative of the desired inlet temperature of the catalyst bed 27. In response to signals 133 and 135, the temperature controller 134 establishes an output signal 136 which is responsive to the difference between signals 133 and 135. Signal 136 is provided from the temperature controller 134 as an input to the I/P transducer 137. Signal 136 is converted from electrical form to pneumatic form by the I/P transducer 137 and is provided as signal 138 to the pneumatic control valve 139 which is operably located in conduit means 57. The pneumatic control valve 139 is manipulated in response to signal 138 to thereby maintain the inlet temperature of the catalyst bed 27 substantially equal to the desired inlet temperature represented by the set point signal 135.

Temperature transducer 141, in combination with a temperature sensing device such as a thermocouple which is operably located in the reactor 22, provides an output signal 143 which is representative of the inlet temperature of the catalyst bed 28. Signal 143 is provided as the process variable input to the temperature controller 144. The temperature controller 144 is also provided with a set point signal 145 which is representative of the desired inlet temperature of the catalyst bed 28. In response to signals 143 and 145, the temperature controller 144 establishes an output signal 146 which is responsive to the difference between signals 143 and 145. Signal 146 is provided from the temperature controller 144 as an input to the I/P transducer 147. Signal 146 is converted from electrical form to pneumatic form by the I/P transducer 147 and is provided as signal 148 to the pneumatic control valve 149 which is operably located in conduit means 58. The pneumatic control valve 149 is manipulated in response to signal 148 to thereby maintain the inlet temperature of the catalyst bed 28 substantially equal to the desired inlet temperature represented by the set point signal 145.

Temperature transducer 151, in combination with a temperature sensing device such as a thermocouple which is operably located in conduit means 37, provides an output signal 153 which is representative of the temperature of the overhead stream flowing from the fractionator 33. Signal 153 is provided as the process variable input to the temperature controller 154. The temperature controller 154 is also provided with a set point signal 155 which is representative of the desired temperature of the overhead stream flowing from the fractionator 33. In response to signals 153 and 155, the temperature controller 154 establishes an output signal 156 which is responsive to the difference between signals 153 and 155. Signal 156 is provided from the temperature controller 154 as an input to the I/P transducer 157. Signal 156 is converted from electrical form to pneu-matic form by the I/P transducer 157 and is provided as signal 158 to the pneumatic control valve 159 which is operably located in conduit means 53. The pneumatic control valve 159 is manipulated in response to signal 158 to thereby maintain the temperature of the overhead stream flowing from the fractionator 33 substantially equal to the desired inlet temperature represented by the set point signal 155.

Flow transducer 161, in combination with flow sensor 162 which is operably located in conduit means 34, provides an output signal 164 which is representative of the flow rate of the heating fluid flowing through conduit means 34. Signal 164 is provided as a process variable input to the flow controller 165. The flow controller 165 is also provided with a set point signal 167 which is representative of the desired flow rate of the heating fluid flowing through conduit means 34. In response to signals 164 and 167, the flow controller 165 establishes an output signal 168 which is responsive to the difference between signals 164 and 167. Signal 168 is provided as a control signal to the pneumatic control valve 169 which is operably located in conduit means 34. The pneumatic control valve 169 is manipulated in response to signal 168 to thereby maintain the actual flow rate of the heating fluid flowing through conduit means 34 substantially equal to the desired flow rate represented by signal 167.

Level controller 171 establishes an output signal 172 which is scaled so as to be representative of the flow rate of the fluid flowing through conduit means 51 required to maintain the desired liquid level in the accumulator 44. Signal 172 is provided as the set point signal to the flow controller 174. Flow transducer 175, in combination with flow sensor 176 which is operably located in conduit means 51, provides an output signal 177 which is representative of the flow rate of the fluid flowing through conduit means 51. Signal 177 is provided as the process variable input to the flow controller 174. In response to signals 172 and 177, the flow controller 174 establishes an output signal 178 which is responsive to the difference between signals 172 and 177. Signal 178 is provided as a control signal from the flow controller 174 to the pneumatic control valve 179 which is operably located in conduit means 51. Pneumatic control valve 179 is manipulated in response to signal 178 to thereby maintain a desired liquid level in the accumulator 44.

The temperature profile across reactor 22 is typically maintained in the range of about 130° F. to about 150° F. Preferably, the inlet temperature is maintained at a temperature of about 130° F. and thus signal 125 will typically be representative of about 130° F. The feed flowing through conduit means 13 is preferably split substantially equally between conduit means 15 and conduit means 24. For a total feed flow rate through conduit means 13 on the order of about two million pounds per day, the outlet temperature of the first catalyst bed 25 will be about 144° F. where the inlet temperature is maintained at about 130° F. The feed flowing through conduit means 24 will typically have a temperature of about 90° F. Combining the feed flowing through conduit means 24 with the reaction effluent flowing from the catalyst bed 25 provides an inlet temperature into the catalyst bed 26 of about 130° F.

The fluid flowing through conduit means 56 will typically have a temperature of about 100° F. The flow rate of the fluid flowing through conduit means 57 and 58 is manipulated so as to maintain a desired inlet temperature to the catalyst beds 27 and 28. If the inlet temperatures of catalyst beds 27 and 28 are maintained at about 130° F., the outlet temperature of the reactor 22 will typically be about 142° F. The use of the split feed stream and the recycle stream to control the temperature profile across the reactor 22 insures a close control of the temperature profile across each catalyst bed in the reactor 22 and thus insures the close control of the total temperature profile across the reactor 22.

Generally, the ratio of methanol to isobutylene in the feed flowing through conduit means 13 will be in the range of about 1.1:1 to about 1.2:1. Where the ratio of methanol to isobutylene in the feed stream flowing through conduit means 13 is in this range, the ratio of methanol to isobutylene in the effluent flowing through conduit means 31 will typically be in the range of about 2:1 to about 3:1 for a conversion percentage of about 90 percent. A methanol to isobutylene ratio of 1.1:1 is presently preferred. For this ratio, the set point signal 76 will be set at a ratio of methanol to isobutylene of 2:1 assuming a percentage conversion of 90 percent.

It is particularly advantageous to analyze the effluent flowing from the reactor 31 to maintain the desired ratio because the ratio of methanol to isobutylene will be substantially greater in the effluent flowing through conduit means 31 than in the feed flowing through conduit means 13. The accuracy of the ratio control is thus improved by basing the control on the analysis of the effluent stream flowing from the reactor 31 rather than utilizing only the analysis of the feed stream flowing through conduit means 13 to control the ratio of methanol to isobutylene in the feed flowing through conduit means 13.

The invention has been described in terms of a presently preferred embodiment as is illustrated in FIG. 1. Specific components which can be used in the practice of the invention as illustrated in FIG. 1 such as flow sensors 62, 94, 102, 176 and 162; flow transducers 61, 93, 101, 175 and 161; flow controllers 64, 91, 165, 174, and 105; pneumatic control valves 97, 68, 109, 129, 119, 139, 149, 159, 179 and 169; current to pressure transducers 85, 127, 113, 137, 147, and 157; temperature transducers 121, 131, 141, and 151; temperature controllers 144, 134, 144 and 154; pressure transducer 111; pressure controller 116; level controller 171; and analyzer controllers 175 and 179 are each well known, commercially available control components such as are described at length in Perrys Chemical Engineers Handbook, 4th Edition, Chapter 22, McGraw Hill.

Analyzer transducers 71 and 81 are preferably chromotographic analyzers such as the Model 102 process chromatograph system, manufactured by Applied Automation, Inc., Bartlesville, Ok. For reasons of brevity, conventional auxiliary equipment such as pumps, additional heat exchangers, additional measurement-control devices, etc. have not been included in the above description as they play no part in the explanation of the invention.

While the invention has been described in terms of the presently preferred embodiment, reasonable variations and modifications are possible by those skilled in the art, within the scope of the described invention and the appended claims. Variations such as utilizing the control system of the present invention in different processes or in conjunction with reactors which contain less than or more than four catalyst beds is within the scope of the invention.

That which is claimed is:

1. Apparatus comprising:
   a reactor having at least first, second and third catalyst beds in series;
   a first heat exchange means;
   means for supplying a first portion of a feed stream through said first heat exchange means to said reactor at a point prior to said first catalyst bed;
   means for supplying a heating fluid to said first heat exchange means to thereby supply heat to said first portion of said feed stream;
   means for supplying a second portion of said feed stream to said reactor at a point after said first catalyst bed but before said second catalyst bed;
   means for supplying a diluent fluid stream to said reactor at a point after said second catalyst bed but before said third catalyst bed;
   means for establishing a first signal representative of the feed inlet temperature of said first catalyst bed;
   means for establishing a second signal representative of the desired feed inlet temperature for said first catalyst bed;
   means for comparing said first signal and said second signal and for establishing a third signal responsive to the difference between said first signal and said second signal;
   means for manipulating the flow rate of said heating fluid to said first heat exchanger means to thereby maintain the actual inlet temperature of said first catalyst bed substantially equal to the desired inlet temperature for said first catalyst bed;
   means for establishing a fourth signal representative of the inlet temperature of said third catalyst bed;
   means for establishing a fifth signal representative of the desired inlet temperature for said third catalyst bed;
   means for comparing said fourth signal and said fifth signal and for establishing a sixth signal responsive to the difference between said fourth signal and said fifth signal; and
   means for manipulating the flow rate of said diluent fluid stream in response to said sixth signal to thereby maintain the actual inlet temperature of said third catalyst bed substantially equal to the desired inlet temperature for said third catalyst bed.

2. Apparatus in accordance with claim 1 additionally comprising:
   means for establishing a seventh signal representative of the flow rate of said first portion of said feed stream;
   means for establishing an eighth signal representative of the desired flow rate for said first portion of said feed stream;
   means for comparing said seventh signal and said eighth signal and for establishing a ninth signal responsive to the difference between said seventh signal and said eighth signal;
   means for manipulating the flow rate of said first portion of said feed stream in response to said ninth signal;
   means for establishing a tenth signal representative of the pressure of said second portion of said feed stream;
   means for establishing an eleventh signal representative of the desired pressure for said second portion of said feed stream;
   means for comparing said tenth signal and said eleventh signal and for establishing a twelfth signal responsive to the difference between said tenth signal and said eleventh signal; and means for manipulating the flow rate of said second portion of said feed stream in response to said twelfth signal, the flow control on said first portion of said feed stream and the pressure control on said second portion of said feed stream maintaining a desired split of said feed stream.

3. Apparatus in accordance with claim 1 additionally comprising:

means for combining a first reactant stream containing a first reactant and a second reactant stream containing a second reactant to form said feed stream;

means for establishing a seventh signal representative of the ratio of said first reactant to said second reactant in the reaction effluent flowing from said reactor;

means for establishing an eighth signal representative of the desired ratio of said first reactant to said second reactant in the reaction effluent flowing from said reactor;

means for comparing said seventh signal and said eighth signal and for establishing a ninth signal responsive to the difference between said seventh signal and said eighth signal, said ninth signal being representative of the ratio of said first reactant to said second reactant in said feed stream required to maintain a desired ratio of said first reactant to said second reactant in the reaction effluent flowing from said reactor;

means for establishing a tenth signal representative of the actual ratio of said first reactant to said second reactant in said feed stream;

means for comparing said ninth signal and said tenth signal and for establishing an eleventh signal responsive to the difference between said ninth signal and said tenth signal, said eleventh signal being representative of the flow rate of said first reactant stream required to maintain a desired ratio of said first reactant to said second reactant in the reaction effluent flowing from said reactor; and means for maintaining a desired ratio of said first reactant to said second reactant in the reaction effluent flowing from said reactor in response to said eleventh signal.

4. Apparatus in accordance with claim 3 wherein said means for maintaining a desired ratio of said first reactant to said second reactant in the reaction effluent flowing from said reactor in response to said eleventh signal comprises:

means for establishing a twelfth signal representative of the actual flow rate of said first reactant stream;

means for comparing said eleventh signal and said twelfth signal and for establishing a thirteenth signal responsive to the difference between said eleventh signal and said twelfth signal;

means for manipulating the flow rate of said first reactant stream in response to said thirteenth signal;

means for establishing a fourteenth signal representative of the actual flow rate of said second reactant stream;

means for establishing a fifteenth signal representative of the desired flow rate of said second reactant stream;

means for comparing said fourteenth signal and said fifteenth signal and for establishing a sixteenth signal responsive to the difference between said fourteenth signal and said fifteenth signal; and means for manipulating the flow rate of said second reactant stream in response to said sixteenth signal, the combined control of the flow rate of said first reactant stream and the flow rate of said second reactant stream maintaining a desired ratio of said first reactant to said second reactant in the reaction effluent flowing from said reactor.

5. Apparatus in accordance with claim 1 wherein said means for supplying said diluent fluid to said reactor comprises:

a fractional distillation column means;

means for withdrawing the reaction effluent from said reactor and for supplying said reaction effluent to said fractional distillation column means;

a second heat exchanger means;

an overhead accumulator means;

means for withdrawing an overhead stream from said fractional distillation column means and for supplying said overhead stream through said second heat exchanger means to said overhead accumulator means; and means for supplying at least a portion of the liquid in said overhead accumulator means to said reactor as said diluent fluid stream.

6. Apparatus in accordance with claim 5 additionally comprising:

a fourth catalyst bed in said reactor;

means for supplying at least a portion of the liquid in said overhead accumulator means to said reactor at a point after said third catalyst bed but before said fourth catalyst bed;

means for establishing a seventh signal representative of the feed inlet temperature of said fourth catalyst bed;

means for establishing an eighth signal representative of the desired feed inlet temperature for said fourth catalyst bed;

means for comparing said seventh signal and said eighth signal and for establishing a ninth signal responsive to the difference between said seventh signal and said eighth signal; and means for manipulating the flow rate of the liquid flowing from said overhead accumulator means to said reactor at a point after said third catalyst bed but before said fourth catalyst bed in response to said ninth signal to thereby maintain the actual feed inlet temperature of said fourth catalyst bed substantially equal to the desired feed inlet temperature for said fourth catalyst bed.

7. A method for controlling the temperature profile across a reactor which contains at least first, second and third reaction zones, wherein the effluent flowing from said first reaction zone flows to said second reaction zone, wherein the effluent flowing from said second reaction zone flows to said third reaction zone, wherein a first portion of a feed stream is provided to said first reaction zone, wherein a second portion of said feed stream is provided to said second reaction zone, and wherein a diluent fluid is provided to said third reaction zone, said method comprising the steps of:

establishing a first signal representative of the feed inlet temperature of said first reaction zone;

establishing a second signal representative of the desired feed inlet temperature for said first reaction zone;

comparing said first signal and said second signal and establishing a third signal responsive to the difference between said first signal and said second signal;

manipulating the temperature of said first portion of said feed stream in response to said third signal to thereby maintain the actual feed inlet temperature of said first reaction zone substantially equal to the desired feed inlet temperature for said first reaction zone;

establishing a fourth signal representative of the feed inlet temperature of said third reaction zone;

establishing a fifth signal representative of the desired feed inlet temperature for said third reaction zone;

comparing said fourth signal and said fifth signal and establishing a sixth signal responsive to the difference between said fourth signal and said fifth signal; and manipulating the flow rate of said diluent fluid to said third reaction zone to thereby maintain the actual feed inlet temperature of said third reaction zone substantially equal to the desired feed inlet temperature for said third reaction zone.

8. A method in accordance with claim 7 additionally comprising the steps of:

establishing a seventh signal representative of the flow rate of said first portion of said feed stream;

establishing an eighth signal representative of the desired flow rate for said first portion of said feed stream;

comparing said seventh signal and said eighth signal and establishing a ninth signal responsive to the difference between said seventh signal and said eighth signal;

manipulating the flow rate of said first portion of said feed stream in response to said ninth signal;

establishing a tenth signal representative of the pressure of said second portion of said feed stream;

establishing an eleventh signal representative of the desired pressure for said second portion of said feed stream;

comparing said tenth signal and said eleventh signal and establishing a twelfth signal responsive to the difference between said tenth signal and said eleventh signal; and manipulating the flow rate of said second portion of said feed stream in response to said twelfth signal, the flow control on said first portion of said feed stream and the pressure control on second portion of said feed stream maintaining a desired split of said feed stream.

9. A method in accordance with claim 7 additionally comprising the steps of:

combining a first reactant stream containing a first reactant with a second reactant stream containing a second reactant to produce said feed stream;

establishing a seventh signal representative of the ratio of said first reactant to said second reactant in the reaction effluent flowing from said reactor;

establishing an eighth signal representative of the desired ratio of said first reactant to said second reactant in the reaction effluent flowing from said reactor;

comparing said seventh signal and said eighth signal and establishing a ninth signal responsive to the difference between said seventh signal and said eighth signal, said ninth signal being representative of the ratio of said first reactant to said second reactant in said feed stream required to maintain a desired ratio of said first reactant to said second reactant in the reaction effluent flowing from said reactor;

establishing a tenth signal representative of the actual ratio of said first reactant to said second reactant in said feed stream;

comparing said ninth signal and said tenth signal and establishing an eleventh signal responsive to the difference between said ninth signal and said tenth signal, said eleventh signal being representative of the flow rate of said first reactant stream required to maintain a desired ratio of said first reactant to said second reactant in the reaction effluent flowing from said reactor; and maintaining a desired ratio of said first reactant to said second reactant in the reaction effluent flowing from said reactor in response to said eleventh signal.

10. A method in accordance with claim 9 wherein said step of maintaining a desired ratio of said first reactant to said second reactant in the reaction effluent flowing from said reactor in response to said eleventh signal comprises:

establishing a twelfth signal representative of the actual flow rate of said first reactant stream;

comparing said eleventh signal and said twelfth signal and establishing a thirteenth signal responsive to the difference between said eleventh signal and said twelfth signal;

manipulating the flow rate of said first reactant stream in response to said thirteenth signal;

establishing a fourteenth signal representative of the actual flow rate of said second reactant stream;

establishing a fifteenth signal representative of the desired flow rate for said second reactant stream;

comparing said fourteenth signal and said fifteenth signal and establishing a sixteenth signal responsive to the difference between said fourteenth signal and said fifteenth signal; and manipulating the flow rate of said second reactant stream in response to said sixteenth signal, the combined control of the flow rate of said first reactant stream and the flow rate of said second reactant stream maintaining a desired ratio of said first reactant to said second reactant in said reaction effluent flowing from said reactor.

11. A method in accordance with claim 7 wherein said step of supplying said diluent fluid to said third reaction zone comprises:

withdrawing the reaction effluent from said reactor and supplying the reaction effluent withdrawn from said reactor to a fractional distillation zone;

withdrawing an overhead stream from said fractional distillation zone and supplying said overhead stream to an overhead accumulation zone; and supplying at least a portion of the liquid in said overhead accumulation zone to said third reaction zone as said diluent fluid.

12. A method in accordance with claim 11 additionally comprising the steps of:

supplying at least a portion of the liquid in said overhead accumulation zone to a fourth reaction zone in said reactor as a diluent fluid;

establishing a seventh signal representative of the feed inlet temperature of said fourth reaction zone;

establishing an eighth signal representative of the desired feed inlet temperature for said fourth reaction zone;

comparing said seventh signal and said eighth signal and establishing a ninth signal responsive to the difference between said seventh signal and said eighth signal; and manipulating the flow rate of the liquid flowing from said overhead accumulation zone to said fourth reaction zone in response to said ninth signal to thereby maintain the actual feed inlet temperature of said fourth reaction zone substantially equal to the desired feed inlet temperature for said fourth reaction zone.

13. Apparatus comprising:

a reactor;

means for combining at least a first reactant stream containing a first reactant and a second reactant stream containing a second reactant to form a feed stream;

means for supplying said feed stream to said reactor;

means for withdrawing the reaction effluent from said reactor;

means for establishing a first signal representative of the ratio of said first reactant to said second reactant in the reaction effluent flowing from said reactor;

means for establishing a second signal representative of the desired ratio of said first reactant to said second reactant in the reaction effluent flowing from said reactor;

means for comparing said first signal and said second signal and for establishing a third signal responsive to the difference between said first signal and said second signal, said third signal being representative of the ratio of said first reactant to said second reactant in said feed stream required to maintain a desired ratio of said first reactant to said second reactant in the reaction effluent flowing from said reactor;

means for establishing a fourth signal representative of the actual ratio of said first reactant to said second reactant in said feed stream;

means for comparing said third signal and said fourth signal and for establishing a fifth signal responsive to the difference between said third signal and said fourth signal, said fifth signal being representative of the flow rate of said first reactant stream required to maintain a desired ratio of said first reactant to said second reactant in the reaction effluent flowing from said reactor; and means for maintaining a desired ratio of said first reactant to said second reactant in the reaction effluent flowing from said reactor in response to said fifth signal.

14. Apparatus in accordance with claim 13 wherein said means for maintaining a desired ratio of said first reactant to said second reactant in the reaction effluent flowing from said reactor in response to said fifth signal comprises:

means for establishing a sixth signal representative of the actual flow rate of said first reactant stream;

means for comparing said fifth signal and said sixth signal and for establishing a seventh signal responsive to the difference between said fifth signal and said sixth signal;

means for manipulating the flow rate of said first reactant stream in response to said seventh signal;

means for establishing an eighth signal representative of the actual flow rate of said second reactant stream;

means for establishing a ninth signal representative of the desired flow rate of said second reactant stream;

means for comparing said eighth signal and said ninth signal and for establishing a tenth signal responsive to the difference between said eighth signal and said ninth signal; and means for manipulating the flow rate of said second reactant stream in response to said tenth signal, the combined control of the flow rate of said first reactant stream and the flow rate of said second reactant stream maintaining a desired ratio of said first reactant to said second reactant in the reaction effluent flowing from said reactor.

15. A method for controlling the ratio of at least two reactants in a feed stream flowing to a reaction zone wherein at least a first reactant stream containing a first reactant and a second reactant stream containing a second reactant are combined to form said feed stream, said method comprising the steps of:

establishing a first signal representative of the ratio of said first reactant to said second reactant in the reaction effluent flowing from said reaction zone;

establishing a second signal representative of the desired ratio of said first reactant to said second reactant in the reaction effluent flowing from said reaction zone;

comparing said first signal and said second signal and establishing a third signal responsive to the difference between said first signal and said second signal, said third signal being representative of the ratio of said first reactant to said second reactant in said feed stream required to maintain a desired ratio of said first reactant to said second reactant in the reaction effluent flowing from said reaction zone;

establishing a fourth signal representative of the actual ratio of said first reactant to said second reactant in said feed stream;

comparing said third signal and said fourth signal and establishing a fifth signal responsive to the difference between said third signal and said fourth signal, said fifth signal being representative of the flow rate of said first reactant stream required to maintain a desired ratio of said first reactant to said second reactant in said reaction effluent flowing from said reaction zone; and maintaining a desired ratio of said first reactant to said second reactant in the reaction effluent flowing from said reaction zone in response to said fifth signal.

16. A method in accordance with claim 15 wherein said step of maintaining a desired ratio of said first reactant to said second reactant in the reaction effluent flowing from said reaction zone in response to said fifth signal comprises:

establishing a sixth signal representative of the actual flow rate of said first reactant stream;

comparing said fifth signal and said sixth signal and establishing a seventh signal responsive to the difference between said fifth signal and said sixth signal;

manipulating the flow rate of said first reactant stream in response to said seventh signal;

establishing an eighth signal representative of the actual flow rate of said second reactant stream;

establishing a ninth signal representative of the desired flow rate for said second reactant stream;

comparing said eighth signal and said ninth signal and establishing a tenth signal responsive to the difference between said eighth signal and said ninth signal; and manipulating the flow rate of said second reactant stream in response to said tenth signal, the combined control of the flow rate of said first reactant stream and the flow rate of said second reactant stream maintaining a desired ratio of said first reactant to said second reactant in the reaction effluent flowing from said reaction zone.

* * * * *